United States Patent
Leal et al.

(10) Patent No.: US 11,505,516 B2
(45) Date of Patent: Nov. 22, 2022

(54) USE OF MTBE RAFFINATE IN THE PRODUCTION OF PROPYLENE

(71) Applicant: SABIC Global Technologies B.V., Bergen op Zoom (NL)

(72) Inventors: Guillermo Leal, Riyadh (SA); Mohammed Bismillah Ansari, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/631,633

(22) PCT Filed: Jul. 17, 2018

(86) PCT No.: PCT/IB2018/055311
§ 371 (c)(1),
(2) Date: Jan. 16, 2020

(87) PCT Pub. No.: WO2019/016710
PCT Pub. Date: Jan. 24, 2019

(65) Prior Publication Data
US 2020/0140356 A1  May 7, 2020

Related U.S. Application Data

(60) Provisional application No. 62/534,538, filed on Jul. 19, 2017.

(51) Int. Cl.
*C07C 6/04* (2006.01)
*C07C 5/25* (2006.01)
(Continued)

(52) U.S. Cl.
CPC .................. *C07C 6/04* (2013.01); *C07C 5/25* (2013.01); *C07C 7/04* (2013.01); *C07C 7/13* (2013.01);
(Continued)

(58) Field of Classification Search
None
See application file for complete search history.

(56) References Cited

U.S. PATENT DOCUMENTS 3,217,059 A * 11/1965 Linn ...................... C07C 5/2543
585/669
4,282,389 A * 8/1981 Droste .................... C07C 41/06
568/697

(Continued)

FOREIGN PATENT DOCUMENTS

CN   101279879 A   10/2008
CN   102070391 A   5/2011
(Continued)

OTHER PUBLICATIONS

Streich et al., Secure the best benefit from C4 hydrocarbon process—Part 2: Economic evaluation, Hydrocarbon Processing—Process Engineering and Optimization, Jul. 2016, pp. 61-65 (Year: 2016).*

(Continued)

*Primary Examiner* — Philip Y Louie
(74) *Attorney, Agent, or Firm* — Norton Rose Fulbright US LLP (57) ABSTRACT

Systems and methods for producing propylene using an MTBE synthesis raffinate are disclosed. An MTBE synthesis raffinate stream first passes through a molecular sieve to separate n-butane and isobutane from the rest of $C_4$ hydrocarbons of the MTBE synthesis raffinate. The 1-butene in the rest of $C_4$ hydrocarbons of the MTBE synthesis raffinate is then isomerized to form 2-butene. Therefore, the concentration of 2-butene in the subsequent propylene production process increases due to the separation of n-butane and isobutane and the isomerization of 1-butene, resulting in an improved reaction rate and reaction efficiency for propylene production.

19 Claims, 2 Drawing Sheets

(51) Int. Cl.
  *C07C 7/04* (2006.01)
  *C07C 7/13* (2006.01)
  *C07C 41/06* (2006.01)
  *C07C 9/12* (2006.01)
  *C07C 11/06* (2006.01)

(52) U.S. Cl.
  CPC ............... *C07C 9/12* (2013.01); *C07C 11/06* (2013.01); *C07C 2521/10* (2013.01)

(56) References Cited

U.S. PATENT DOCUMENTS

| | | | |
|---|---|---|---|
| 5,300,718 A | 4/1994 | McCaulley | 585/324 |
| 5,670,703 A | 9/1997 | Barendregt et al. | 585/324 |
| 5,898,091 A | 4/1999 | Chodorge et al. | 585/647 |
| 6,225,518 B1 * | 5/2001 | Sohn | C10G 25/12 585/827 |
| 6,414,210 B1 * | 7/2002 | Pirovano | C07C 7/152 585/805 |
| 6,977,318 B2 | 12/2005 | Bridges | 585/324 |
| 2006/0089517 A1 | 4/2006 | Podrebarac et al. | 585/643 |
| 2008/0312481 A1 * | 12/2008 | Leyshon | C07C 6/04 585/324 |
| 2009/0043144 A1 * | 2/2009 | Leyshon | C07C 11/18 585/671 |
| 2009/0112032 A1 | 4/2009 | Eng | 585/324 |
| 2009/0112039 A1 | 4/2009 | Eng | 585/651 |
| 2009/0270665 A1 * | 10/2009 | Magalhaes Mendes | B01D 71/028 585/259 |
| 2011/0282120 A1 * | 11/2011 | Buchanan | C07C 37/08 585/323 |
| 2013/0066032 A1 | 3/2013 | Chewter et al. | 526/351 |
| 2015/0231529 A1 * | 8/2015 | Akolekar | B01J 20/28057 210/643 |
| 2017/0252720 A1 * | 9/2017 | Odeh | C08K 5/56 |

FOREIGN PATENT DOCUMENTS

| | | |
|---|---|---|
| CN | 101555197 B | 1/2013 |
| CN | 102906053 A | 1/2013 |
| EP | 0708070 A1 | 4/1996 |
| WO | WO2008153643 A1 | 12/2008 |
| WO | WO-2011037820 A1 * | 3/2011 ........... B01D 69/142 |

OTHER PUBLICATIONS

International Search Report and Written Opinion from PCT/IB2018/055311 dated Nov. 7, 2018, 10 pages.
Torek, C. H. "Upgrading Ethylene Plant Coproducts." World Petroleum Congress, [H]2 (1994) 8 pages.

* cited by examiner

USE OF MTBE RAFFINATE IN THE PRODUCTION OF PROPYLENE

CROSS REFERENCE TO RELATED APPLICATIONS

This application is a national phase application under 35 U.S.C. § 371 of International Application No. PCT/IB2018/055311 filed Jul. 17, 2018, which claims priority to U.S. Provisional Patent Application No. 62/534,538 filed Jul. 19, 2017. The entire contents of each of the above-referenced disclosures is specifically incorporated by reference herein without disclaimer.

FIELD OF INVENTION

The present invention generally relates to propylene production. More specifically, the present invention relates to methods of producing propylene using methyl tertiary butyl ether (MTBE) synthesis raffinate and ethylene.

BACKGROUND OF THE INVENTION

Steam cracking is one of the most commonly used petrochemical processes. Steam cracking is used to produce major products such as ethylene and propylene, and in such processes, steam cracking also generates byproduct streams that typically contain mixed $C_4$ hydrocarbons. In general, the $C_4$ mixture from the byproduct stream of steam cracking includes various amounts of valuable products such as n-butane, isobutane, isobutylene, 1-butene, 2-butene, butadiene and acetylene. However, currently, a large part of the byproduct stream from steam crackers are used as low value products. In almost all the steam cracking facilities, the only two $C_4$ byproducts that are collected or utilized in subsequent chemical production processes are butadiene, which is separated via solvent extraction, and isobutylene, which is consumed in the process of methyl tertiary butyl ether (MTBE) production.

In the process of MTBE production, a $C_4$ byproduct stream from steam crackers is mixed with methanol and flowed to an ether reactor. Isobutylene in the $C_4$ mixture reacts with methanol to produce methyl tertiary butyl ether (MTBE). The reaction products are then separated via a distillation column. The purified MTBE is collected from the bottom stream of the distillation column. The MTBE synthesis raffinate comprising unreacted $C_4$ mixture (MTBE raffinate) is collected from the top fraction of the distillation column and often used as liquefied petroleum gas. Thus, these $C_4$ byproducts are essentially wasted. Therefore, improvements that take advantage of $C_4$ byproduct streams from steam crackers or $C_4$ raffinate from MTBE production are desired.

BRIEF SUMMARY OF THE INVENTION

A method has been discovered for producing propylene. By using the raffinate from the methyl tertiary butyl ether (MTBE) synthesis as a feed stream to produce propylene, the utilization rate of the $C_4$ byproducts from a steam cracker can be increased. Further, by separating n-butane and isobutane from MTBE synthesis raffinate and isomerizing 1-butene from the MTBE synthesis raffinate, a feed stream with higher 2-butene can be achieved, which in turn can result in higher efficiency in propylene production.

Embodiments of the invention include a method of producing propylene. The method may include flowing a methyl tertiary butyl ether synthesis raffinate stream that comprises $C_4$ hydrocarbons through a molecular sieve so that the molecular sieve separates the MTBE synthesis raffinate into a stream comprising primarily n-butane and isobutane, collectively, and a stream comprising primarily 1-butene and 2-butene, collectively. Further, the stream comprising primarily 1-butene and 2-butene may be distilled to produce a first stream, comprising primarily 1-butene, and a first 2-butene stream, comprising primarily 2-butene. The 1-butene in the first stream may be isomerized to form a second 2-butene stream comprising primarily 2-butene. The method may further include reacting 2-butene of the second 2-butene stream and 2-butene of the first 2-butene stream with ethylene to produce the propylene.

Embodiments of the invention include a method of producing propylene. The method may include flowing a methyl tertiary butyl ether synthesis raffinate stream comprising n-butane, isobutane, 1-butene, and 2-butene through a molecular sieve so that the molecular sieve separates the MTBE synthesis raffinate into a stream comprising primarily n-butane and isobutane, collectively, and a stream comprising primarily 1-butene and 2-butene, collectively. The molecular sieve may comprise zeolite (e.g., Zeolite-X with a formula of $Na_{88}Al_{88}Si_{104}O_{384} \cdot 220H_2O$). Furthermore, the stream comprising primarily 1-butene and 2-butene may be distilled to produce a first stream, comprising primarily 1-butene, and a first 2-butene stream, comprising primarily 2-butene. The 1-butene in the first stream may be isomerized to form a third stream comprising primarily 2-butene. The method may further include reacting 2-butene of the first 2-butene stream and 2-butene of the second 2-butene stream with ethylene to produce the propylene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The term "$C_n+$" or "$C_n+$ hydrocarbon", wherein n is a positive integer, e.g. 1, 2, 3, 4, or 5, as that term is used in the specification and/or claims, means any hydrocarbon having at least n number of carbon atom(s) per molecule.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, at least twenty embodiments are now described. Embodiment 1 relates to a method of producing propylene. The method includes the steps of flowing a methyl tertiary butyl ether (MTBE) synthesis raffinate stream that contains $C_4$ hydrocarbons through a molecular sieve so that the molecular sieve separates the MTBE synthesis raffinate stream into a stream comprising primarily n-butane and isobutane, collectively, and a stream comprising primarily 1-butene and 2-butene, collectively; distilling the stream comprising primarily 1-butene and 2-butene collectively to produce a first stream comprising primarily 1-butene and a first 2-butene stream comprising primarily 2-butene; isomerizing the 1-butene in the first stream to form a second 2-butene stream comprising primarily 2-butene; and reacting 2-butene of the first 2-butene stream and 2-butene of the second 2-butene stream with ethylene to produce the propylene. Embodiment 2 is the method of embodiment 1, wherein the $C_4$ hydrocarbons are selected from the group consisting of n-butane, isobutane, 1-butene, 2-butene, and combinations thereof. Embodiment 3 is the method of embodiment 1, wherein the $C_4$ hydrocarbons are from a byproduct stream of a steam cracker unit, the byproduct stream comprising hydrocarbons selected from the group consisting of n-butane, isobutane, isobutylene, 1-butene, 2-butene, butadiene, acetylene, and combinations thereof. Embodiment 4 is the method of any of embodiments 1 to 3, wherein the molecular sieve comprises zeolite. Embodiment 5 is the method of embodiment 4, wherein the zeolite is selected from the group consisting of zeolite X, zeolite Y, ZSM-5, silicalite-1, and combinations thereof. Embodiment 6 is the method of any of embodiments 1 to 5, wherein the molecular sieve comprises a metal-organic framework and the metal-organic framework include zeolitic imidazolate framework-8 (ZIF-8). Embodiment 7 is the method of any of embodiments 1 to 6, wherein the molecular sieve is loaded on a π complexing adsorbent. Embodiment 8 is the method of embodiment 7, wherein the π complexing adsorbents contain a support material selected from the group of consisting of aluminosilicates, silica, alumina, a mesoporous material, and combinations thereof, wherein the mesoporous material includes mesoporous silicas selected from the group consisting of SBA-15, SBA-16, TUD-1 framework type material, or combinations thereof; and a compound supported on the support material, the compound is selected from the group consisting of $AgNO_3$, $CuNO_3$, $Cu(NO_3)_2$, $Fe(NO_3)_2$, and combinations thereof. Embodiment 9 is the method of any of embodiments 1 to 8, wherein the molecular sieve separates 95 wt. % to 99 wt. % of 1-butene and 2-butene, collectively from the MTBE synthesis raffinate. Embodiment 10 is the method of any of embodiments 1 to 9, wherein the separated 1-butene and 2-butene by molecular sieve collectively has a purity in a range of 94.5 wt. % to 99.0 wt. %. Embodiment 11 is the method of any of embodiments 1 to 10, wherein the 2-butene comprises cis-2-butene and trans-2-butene. Embodiment 12 is the method of any of embodiments 1 to 11, wherein the isomerizing is performed in the presence of a first catalyst and the first catalyst is selected from the group consisting of one or more transitional metal elements and/or magnesium oxide. Embodiment 13 is the method of any of embodiments 1 to 12, wherein the isomerizing is performed at a first reaction temperature in a range of 20 to 200° C. Embodiment 14 is the method of any of embodiments 1 to 13, wherein the isomerizing is performed at a first reaction pressure in a range of 0.1 to 2 MPa. Embodiment 15 is the method of any of embodiments 1 to 14, wherein the 1-butene in isomerizing has a gas hourly space velocity in a range of 120 to 350 $hr^{-1}$. Embodiment 16 is the method of any of embodiments 1 to 15, wherein the reacting is performed in the presence of a second catalyst and the second catalyst comprises more transitional elements, and/or magnesium oxide. Embodiment 17 is the method of any of embodiments 1 to 16, wherein the reacting is performed at a second reacting temperature in a range of 270 to 350° C. Embodiment 18 is the method of any of embodiments 1 to 17, wherein the reacting is performed at a second reacting pressure in a range of 300 to 550 Psig. Embodiment 19 is the method of any of embodiments 1 to 18, wherein the reacting is performed at a weight hourly space velocity of 5 to 50 $hr^{-1}$.

Embodiment 20 is a method of producing propylene. This method includes the steps of flowing a methyl tertiary butyl ether (MTBE) synthesis raffinate stream comprising n-butane, isobutane, 1-butene, and 2-butene through a molecular sieve so that the molecular sieve separates the MTBE synthesis raffinate stream into a stream comprising primarily n-butane and isobutane, collectively, and a stream comprising primarily 1-butene and 2-butene, collectively; distilling the stream comprising primarily 1-butene and 2-butene to produce a first stream comprising primarily 1-butene and a first 2-butene stream comprising primarily 2-butene; isomerizing the 1-butene in the first stream to form a second 2-butene stream comprising primarily 2-butene; and reacting 2-butene of the second stream and 2-butene of the first 2-butene stream with ethylene to produce the propylene.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for producing propylene via metathesis using a MTBE synthesis raffinate stream. $C_4$ mixture from naphtha steam cracker may be utilized to first produce MTBE after the separation of butadiene. Then, with a molecular sieve, n-butane and isobutane may be separated from the MTBE synthesis raffinate, thereby increasing the concentration of 1-butene and 2-butene in the remaining $C_4$ mixture from the MTBE synthesis raffinate. The 1-butene in the remaining $C_4$ mixture is then isomerized to form additional 2-butene. Thus, the overall concentration of 2-butene in the metathesis process increases when the n-butane and isobutane are separated from the MTBE synthesis raffinate. Consequently, the reaction rate for propylene production via metathesis of 2-butene and ethylene increases and thereby improves the efficiency of the propylene production process.

Figure 1:
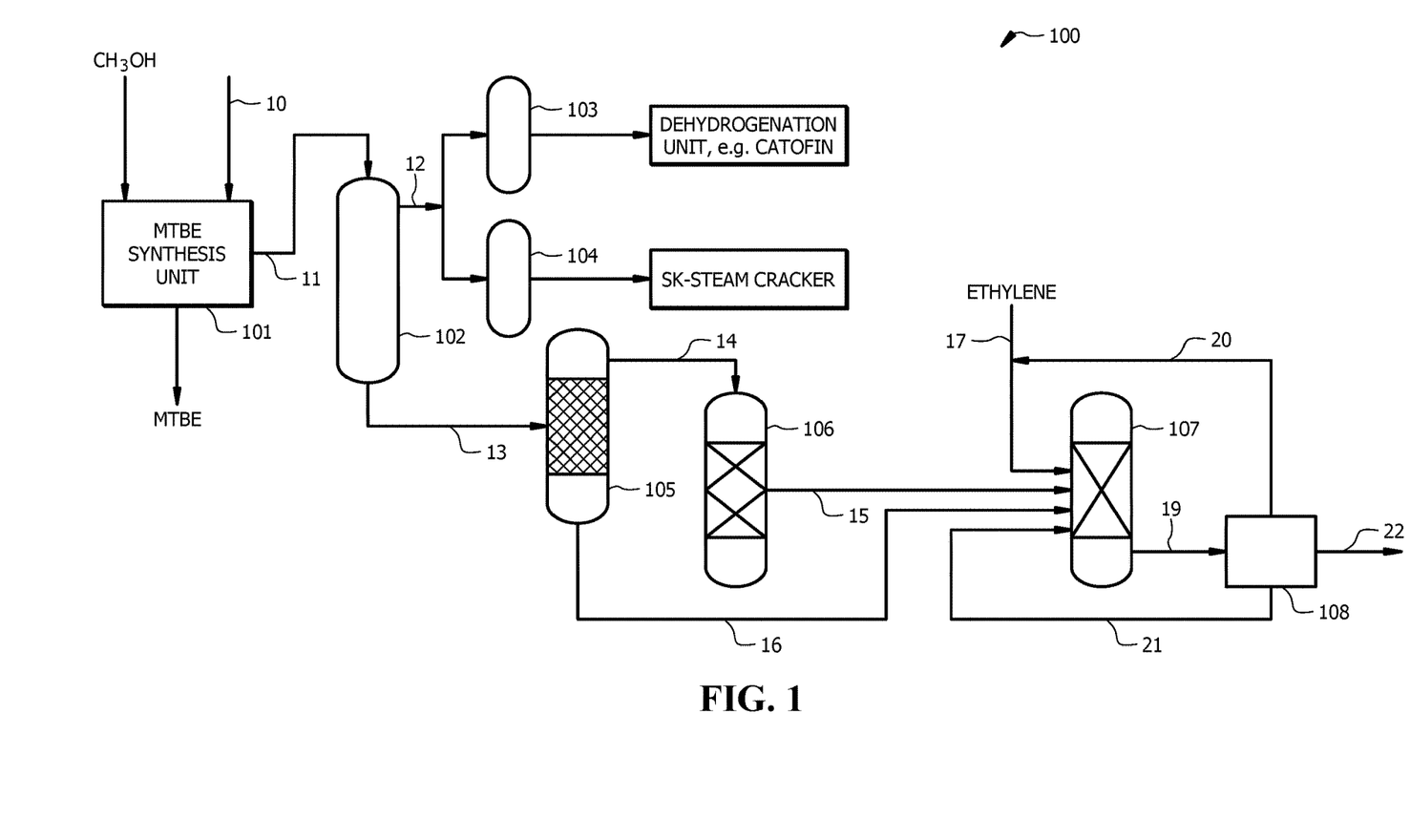
FIG. 1 shows a schematic diagram of a system for producing propylene using MTBE synthesis raffinate, according to embodiments of the invention.

With reference to FIG. 1, a schematic diagram is shown of propylene production system 100, according to embodiments of the invention. Propylene production system 100 may utilize a $C_4$ mixture from a naphtha cracking unit. In embodiments of the invention, the $C_4$ mixture from naphtha cracking unit may comprise n-butane, isobutane, isobutylene, 1-butene, 2-butene, butadiene, acetylene, or combinations thereof. The $C_4$ mixture from the naphtha cracking unit may be then flowed through a selective hydrogenation unit to remove acetylene and an extractive distillation column to separate and recover butadiene. The remaining $C_4$ obtained from the extractive distillation column may form $C_4$ hydrocarbons stream 10 used as a feed stream for propylene production system 100. As shown in FIG. 1, according to embodiments of the invention, propylene production system 100 may comprise MTBE synthesis unit 101 that is configured to produce MTBE by consuming isobutylene from $C_4$ hydrocarbons stream 10.

An outlet of MTBE synthesis unit 101 may be in fluid communication with first separation unit 102. In embodiments of the invention, first separation unit 102 may comprise a molecular sieve disposed therein. The raffinate from MTBE synthesis unit 101 may form stream 11, which flows to the molecular sieve in first separation unit 102. According to embodiments of the invention, the molecular sieve may be configured to separate MTBE raffinate in stream 11 into stream 12, comprising primarily butane and isobutane collectively, and stream 13, comprising primarily 1-butene and 2-butene collectively.

According to embodiments of the invention, the molecular sieve in first separation unit 102 may comprise zeolite. Zeolites typically have a general formula of $M_{x/n}[(AlO_2)_x(SiO_2)_y].mH_2O$, where x, y, m and n are positive integers. For example, Zeolite-X has a formula of $Na_{88}Al_{88}Si_{104}O_{384}.220H_2O$. Exemplary zeolites in embodiments of the invention may include, but are not limited to Faujasite type zeolite (e.g. zeolite X, zeolite Y), Mordenite Framework Inverted (MFI) type zeolite (e.g. ZSM-5, Silicalite-1), and combinations thereof. Additionally or alternatively, the molecular sieve may comprise a metal-organic framework. In embodiments of the invention, the metal-organic framework may include zeolitic imidazolate framework-8.

According to embodiments of the invention, molecular sieves may be loaded on π complexing adsorbents. The π complexing adsorbents may include a support material and a compound supported on the support material. In embodiments of the invention, the compound may include a metal nitrate. Exemplary metal nitrates may include, but are not limited to $AgNO_3$, $CuNO_3$, $Cu(NO_3)_2$, $Fe(NO_3)_2$, or combinations thereof. In embodiments of the invention, the support material may include aluminosilicates, silica, alumina, a mesoporous material, and combinations thereof. Exemplary mesoporous materials may include, but are not limited to mesoporous silicas including SBA-15 and SBA-16, TUD-1 framework type materials, or combinations thereof.

In embodiments of the invention, a first outlet of first separation unit 102 is in fluid communication with first isomerization unit 103 and/or hydrogenation unit 104. First isomerization unit 103 may be in fluid communication with a dehydrogenation unit, such as a CATOFIN unit. Product from hydrogenation unit 104 may be recycled to a steam cracker. A second outlet of first separation unit 102 is in fluid communication with distillation column 105. Distillation column 105 may be configured to separate stream 13 (comprising 1-butene and 2-butene) into first stream 14 comprising primarily 1-butene, and first 2-butene stream 16, comprising primarily 2-butene.

According to embodiments of the invention, a top outlet of distillation column 105 may be in fluid communication with second isomerization unit 106. Second isomerization unit 106 may be configured to isomerize the 1-butene of first stream 14 to form second 2-butene stream 15, comprising primarily 2-butene. In embodiments of the invention, a bottom outlet of distillation column 105 may be in fluid communication with an inlet of olefin conversion unit 107. An outlet of second isomerization unit 106 may be in fluid communication with an inlet of olefin conversion unit 107. Second 2-butene stream 15 and first 2-butene stream 16, both of which comprise primarily 2-butene, may be flowed to olefin conversion unit 107. According to embodiments of the invention, ethylene stream 17 comprising primarily ethylene may be configured to flow in olefin conversion unit 107.

In embodiments of the invention, 2-butene of first 2-butene stream 16 and second 2-butene stream 15 may react with ethylene from ethylene stream 17 in olefin conversion unit 107 to produce propylene via metathesis. An outlet of olefin conversion unit 107 may be in fluid communication with second separation unit 108. Second separation unit 108 is configured to separate first product stream 19 that comprises propylene, ethylene, 2-butene from olefin conversion unit 107 into second product stream 22 comprising primarily propylene, unreacted ethylene stream 20 comprising primarily unreacted ethylene, and unreacted 2-butene stream 21 comprising primarily unreacted 2-butene. In embodiments of the invention, unreacted ethylene stream 20 and unreacted 2-butene stream 21 may be recycled back to olefin conversion unit 107.

Figure 2:
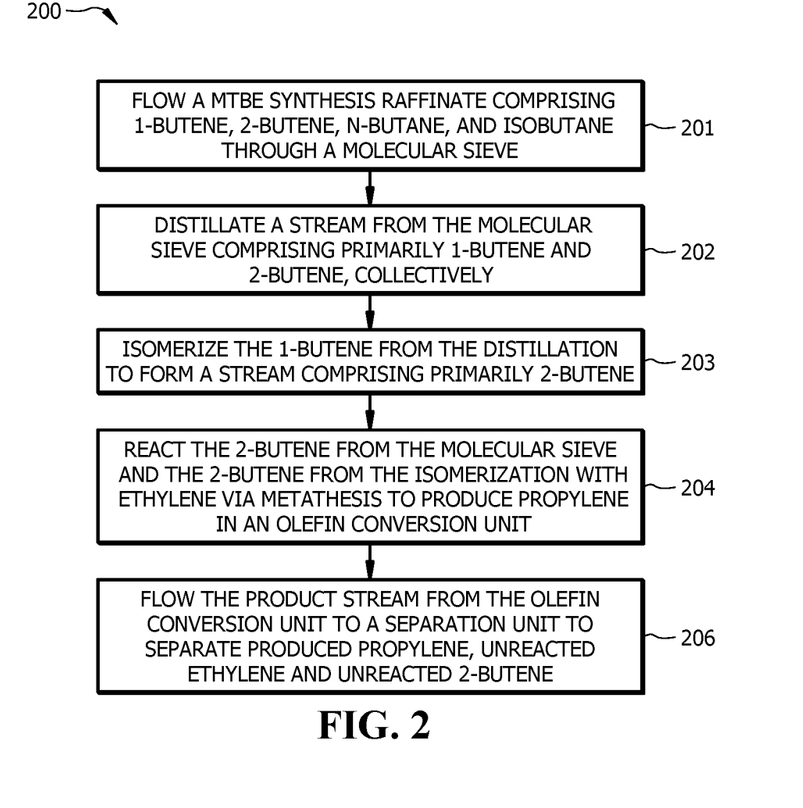
FIG. 2 shows a schematic flowchart for a method of producing propylene using MTBE synthesis raffinate, according to embodiments of the invention.

As shown in FIG. 2, embodiments of the invention include method 200 for producing propylene using raffinate from MTBE synthesis. Method 200 may be implemented by propylene production system 100, as shown in FIG. 1. According to embodiments of the invention, the $C_4$ feedstock of method 200 may be stream 11 that comprises a raffinate from methyl tertiary butyl ether (MTBE) synthesis. In embodiments of the invention, methyl tertiary butyl ether (MTBE) synthesis may comprise the step of reacting methanol with isobutylene from $C_4$ hydrocarbons stream 10 over a catalyst that may comprise an acid type ion exchange resin at reactions conditions sufficient to form MTBE. The reaction conditions may include a reaction temperature in a range of 15° C. to 150° C. and all ranges and values therebetween, including 15° C. to 30° C., 30° C. to 45° C., 45° C. to 60° C., 60° C. to 75° C., 75° C. to 90° C., 90° C. to 105° C., 105° C. to 120° C., 120° C. to 135° C., or 135° C. to 150° C. The reaction conditions may further comprise a reaction pressure in a range of 80 psig to 400 psig and all ranges and values therebetween, including 80 psig to 100 psig, 100 psig to 120 psig, 120 psig to 140 psig, 140 psig to 160 psig, 160 psig to 180 psig, 180 psig to 200 psig, 200 psig to 220 psig, 220 psig to 240 psig, 240 psig to 260 psig, 260 psig to 280 psig, 280 psig to 300 psig, 300 psig to 320 psig, 320 psig to 340 psig, 340 psig to 360 psig, 360 psig to 380 psig, or 380 psig to 400 psig.

According to embodiments of the invention, $C_4$ hydrocarbons stream 10 may be from a byproduct stream of a steam cracker unit. The byproduct stream from the steam cracker unit may comprise 5 to 35 wt. % of n-butane, 1 to 15 wt. % of isobutane, 20 to 50 wt. % of isobutylene, 10 to 35 wt. % of 1-butene, 5 to 20 wt. % of 2-butene, 1 to 3 wt. % of butadiene, and 0 to 1 wt. % of acetylene. In embodiments of the invention, the acetylene in the byproduct stream from the steam cracker unit may be converted to ethylene via selective hydrogenation. The butadiene in the byproduct stream may be converted to butane by hydrogenation. Additionally or alternatively, the butadiene in the byproduct stream may be separated by solvent extraction. In embodiments of the invention, the solvent in the solvent extraction of butadiene may include dimethylformamide, n-methyl-pyrrolidone, acetonitrile, furfural, n-methyl-2-pyrrolidone, acetone, dimethylacetamide, cuprous ammonium acetate, beta-methoxypropionitrile, or combinations thereof.

In embodiments of the invention, the formed MTBE may be purified and excess methanol in the MTBE production process may be separated and recycled back to MTBE production. In embodiments of the invention, as shown in block 201, method 200 includes flowing a methyl tertiary butyl ether (MTBE) synthesis raffinate of stream 11 that comprises 1-butene, 2-butene, n-butane and isobutane through a molecular sieve. According to embodiments of the invention, the molecular sieve separates the MTBE synthesis raffinate into stream 12, comprising primarily n-butane and isobutane, collectively, and stream 13, comprising primarily 1-butene and 2-butene, collectively.

According to embodiments of the invention, the molecular sieve may comprise zeolite. The zeolite may comprise zeolite X, zeolite Y, ZSM-5, silicalite-1, and combinations thereof. Furthermore, the molecular sieve may comprise a metal-organic framework. In embodiments of the invention, exemplary metal organic frameworks may include, but are not limited to zeolitic imidazolate framework-8 (ZIF-8). In embodiments of the invention, the molecular sieve comprises a combination of zeolite and metal-organic framework. According to embodiments of the invention, a pore size of the molecular sieve may be in a range of 4 nm to 6 nm, and all ranges and values therebetween, including 4 nm, 4.5 nm, 5 nm, 5.5 nm, and 6 nm.

In embodiments of the invention, a π complexing adsorbent may be loaded on the molecular sieve. The π complexing adsorbent may comprise a support material that includes aluminosilicates, silica, alumina, a mesoporous material, or combinations thereof. The mesoporous material may include mesoporous silicas comprising SBA-15, SBA-16, TUD-1 framework type materials, or combinations thereof. The π complexing adsorbent may further comprise a metal nitrate supported on the support material. According to embodiments of the invention, the compound supported on the support material may include $AgNO_3$, $CuNO_3$, $Cu(NO_3)_2$, $Fe(NO_3)_2$, or combinations thereof.

According to embodiments of the invention, the separation process of n-butane and isobutane using the molecular sieve can be a vapor phase operation. The operating pressure of the separation process may be constant at 50 to 150 Psig and all ranges and values therebetween including ranges of 50 to 60 Psig, 60 to 70 Psig, 70 to 80 Psig, 80 to 90 Psig, 90 to 100 Psig, 100 to 110 Psig, 110 to 120 Psig, 120 to 130 Psig, 130 to 140 Psig, or 140 to 150 Psig. The operating temperature of the separation process may be in a range of 10 to 150° C. and all ranges and values therebetween including 10 to 20° C., 20 to 30° C., 30 to 40° C., 40 to 50° C., 50 to 60° C., 60 to 70° C., 70 to 80° C., 80 to 90° C., 90 to 100° C., 100 to 110° C., 110 to 120° C., 120 to 130° C., 130 to 140° C., or 140 to 150° C. In embodiments of the invention, the separation process using the molecular sieve is a continuous process. The process of separating n-butane and isobutane from MTBE synthesis raffinate using the molecular sieve, according to the embodiments of the invention, comprises adsorbing the n-butane and isobutane molecules into the molecular sieve structure and rinsing the molecular sieve with desorbents including n-pentane, isopentane, cyclopentane, or combinations thereof, such that the n-butane and isobutane molecules are released from the molecular sieve. Additionally or alternatively, in embodiments of the invention, the n-butane and isobutane may be released from the molecular sieve via change of the operating temperature or pressure.

In embodiments of the invention, by using the molecular sieve, a recovery rate of 1-butene and 2-butene collectively from the MTBE synthesis raffinate may be in a range of 95 wt. % to 99 wt. % and all ranges and values therebetween, including ranges of 95 to 95.2 wt. %, 95.2 to 95.4 wt. %, 95.4 to 95.6 wt. %, 95.6 to 95.8 wt. %, 95.8 to 96.0 wt. %, 96.0 to 96.2 wt. %, 96.2 to 96.4 wt. %, 96.4 to 96.6 wt. %, 96.6 to 96.8 wt. %, 96.8 to 97.0 wt. %, 97.0 to 97.2 wt. %, 97.2 to 97.4 wt. %, 97.4 to 97.6 wt. %, 97.6 to 97.8 wt. %, 97.8 to 98.0 wt. %, 98.0 to 98.2 wt. %, 98.2 to 98.4 wt. %, 98.4 to 98.6 wt. %, 98.6 to 98.8 wt. %, or 98.8 to 99.0 wt. %.

According to embodiments of the invention, stream 13 (comprising primarily 1-butene and 2-butene, collectively) may have a collective purity of 1-butene and 2-butene in a range of 94.5 wt. % to 99.0 wt. % and all ranges and values therebetween, including ranges of 94.5 to 95.0 wt. %, 95.0 to 95.5 wt. %, 95.5 to 96.0 wt. %, 96.0 to 96.5 wt. %, 96.5 to 97.0 wt. %, 97.0 to 97.5 wt. %, 97.5 to 98.0 wt. %, 98.0 to 98.5 wt. %, or 98.5 to 99.0 wt. %. In embodiments of the invention, the 2-butene from the MTBE raffinate may include cis-2-butene and trans-2-butene. In embodiments of the invention, stream 12 comprising n-butane and isobutane is flowed to first isomerization unit 103 followed by a dehydrogenation unit such as fixed bed dehydrogenation reactor (e.g. CATOFIN), fluidized bed dehydrogenation reactor (e.g. FBD-4), moving bed dehydrogenation reactor (e.g. OLEFLEX), or combinations thereof. Alternatively or additionally, stream 12 comprising primarily n-butane and isobutane may be flowed to hydrogenation unit 104 to hydrogenate unsaturated hydrocarbons in stream 12 to form saturated hydrocarbons. The n-butane and the hydrogenated hydrocarbons may be flowed to a steam cracker unit.

In embodiments of the invention, method 200 may further include distilling stream 13 (comprising primarily 1-butene and 2-butene collectively), as shown in block 202. First stream 14 from distillation column 105 may comprise primarily 1-butene. First 2-butene stream 16 from distillation column 105 may comprise primarily 2-butene. According to embodiments of the invention, the operating pressure of the distillation may be in a range of 50 to 150 Psig and all ranges and values therebetween including ranges of 50 to 60 Psig, 60 to 70 Psig, 70 to 80 Psig, 80 to 90 Psig, 90 to 100 Psig, 100 to 110 Psig, 110 to 120 Psig, 120 to 130 Psig, 130 to 140 Psig, or 140 to 150 Psig. In embodiments of the invention, first stream 14 (comprising primarily 1-butene) may be flowed to second isomerization unit 106. Block 203 shows that the 1-butene in first stream 14 from distillation column 105 may be isomerized to form second 2-butene stream 15 (comprising primarily 2-butene).

In embodiments of the invention, the isomerization in block 203 may be performed at a temperature of 20 to 200° C. and all ranges and values therebetween including ranges of 20 to 30° C., 30 to 40° C., 40 to 50° C., 50 to 60° C., 60 to 70° C., 70 to 80° C., 80 to 90° C., 90 to 100° C., 100 to 110° C., 110 to 120° C., 120 to 130° C., 130 to 140° C., 140 to 150° C., 150 to 160° C., 160 to 170° C., 170 to 180° C., 180 to 190° C., or 190 to 200° C. A pressure for isomerization in block 203 may be in a range of 0.1 to 2 MPa and all ranges and values therebetween, including 0.1 MPa, 0.2 MPa, 0.3 MPa, 0.4 MPa, 0.5 MPa, 0.6 MPa, 0.7 MPa, 0.8 MPa, 0.9 MPa, 1.0 MPa, 1.1 MPa, 1.2 MPa, 1.3 MPa, 1.4 MPa, 1.5 MPa, 1.6 MPa, 1.7 MPa, 1.8 MPa, 1.9 MPa, and 2.0 MPa. In embodiments of the invention, isomerization of 1-butene in block 203 may be performed in the presence of a catalyst. Exemplary catalysts for isomerization of 1-butene may include, but are not limited to transitional elements supported on silica, alumina, and/or zeolites. In embodiments of the invention, transitional elements may include any or elements from group 8, group 9, or group 10 of periodic table, or combinations thereof. In embodiments of the invention, the catalyst may further include magnesium oxide. According to embodiments of the invention, the isomerization of 1-butene from first stream 14 may have a gas hourly space velocity of 120 to 350 $hr^{-1}$ and all ranges and values therebetween, including ranges of 120 to 130 $hr^{-1}$, 130 to 140 $hr^{-1}$, 140 to 150 $hr^{-1}$, 150 to 160 $hr^{-1}$, 160 to 170 $hr^{-1}$, 170 to 180 $hr^{-1}$, 180 to 190 $hr^{-1}$, 190 to 200 $hr^{-1}$, 200 to 210 $hr^{-1}$, 210 to 220 $hr^{-1}$, 220 to 230 $hr^{-1}$, 230 to 240 $hr^{-1}$, 240 to 250 $hr^{-1}$, 250 to 260 $hr^{-1}$, 260 to 270 $hr^{-1}$, 270 to 280 $hr^{-1}$, 280 to 290 $hr^{-1}$, 290 to 300 $hr^{-1}$, 300 to 310 $hr^{-1}$, 310 to 320 $hr^{-1}$, 320 to 330 $hr^{-1}$, 330 to 340 $hr^{-1}$, or 340 to 350 $hr^{-1}$.

According to embodiments of the invention, method 200 may further comprise reacting 2-butene of second 2-butene stream 15 and 2-butene of first 2-butene stream 16 with ethylene of ethylene stream 17 to produce the propylene in olefin conversion unit 107 via metathesis, as shown in block 204. In embodiments of the invention, a molar ratio of ethylene to 2-butene feeding to olefin conversion unit 107 may be in a range of 1:1 to 1:1.5 and all ranges and values therebetween, including 1:1, 1:1.1, 1:1.2, 1:1.3, 1:1.4, and 1:1.5. In embodiments of the invention, An ethylene to butene molar ratio in olefin conversion unit 107 may be 0.4:1 to 1.8:1 (typically 0.7:1 to 1.4:1) and all ranges and values therebetween. In embodiments of the invention, the molar ratio of ethylene to 2-butene may be about 1:1.2, which may be used to avoid side reactions and $C_5+$ formation in olefin conversion unit 107.

In embodiments of the invention, the metathesis of 2-butene and ethylene in olefin conversion unit 107 may be performed in the presence of a catalyst. Exemplary catalysts in the metathesis of block 204 may include, but are not limited to one or more transitional elements including tungsten and/or rhenium supported on support material including silica, alumina, or combinations thereof. A co-catalyst including magnesium may be included to further isomerize any 1-butene to 2-butene in olefin conversion unit 107. The metathesis may be at a reaction temperature in a range of 270° C. to 350° C. and all ranges and values therebetween including 270 to 280° C., 280 to 290° C., 290 to 300° C., 300 to 310° C., 310 to 320° C., 320 to 330° C., 330 to 340° C., or 340 to 350° C. Further, according to embodiments of the invention, the metathesis in olefin conversion unit 107 may have a reaction pressure of 350 to 500 Psig (e.g. 425 Psig) and all ranges and values therebetween including 350 Psig, 375 Psig, 400 Psig, 425 Psig, 450 Psig, 475 Psig, or 500 Psig. Olefin conversion unit 107 may have a weight hourly space velocity (based on the weight of the hydrocarbon flowing therein over the weight of the catalyst and support therein) of 5 to 50 $hr^{-1}$ and all ranges and values therebetween including 5 to 10 $hr^{-1}$, 10 to 15 $hr^{-1}$, 15 to 20 $hr^{-1}$, 20 to 25 $hr^{-1}$, 25 to 30 $hr^{-1}$, 30 to 35 $hr^{-1}$, 35 to 40 $hr^{-1}$, 40 to 45 $hr^{-1}$, or 45 to 50 $hr^{-1}$. In embodiments of the invention, the weight hourly space velocity in olefin conversion unit 107 may be in a range of 10 to 25 (typically 15.6) and all ranges and values therebetween.

In embodiments of the invention, first product stream 19 from olefin conversion unit 107 may be flowed to second separation unit 108, as shown in block 205. First product stream 19 may comprise unreacted ethylene, unreacted 2-butene and propylene. According to embodiments of the invention, first product stream 19 may be separated into unreacted ethylene stream 20 comprising primarily unreacted ethylene, unreacted 2-butene stream 21 comprising primarily unreacted 2-butene, and second product stream 22 comprising primarily formed propylene in olefin conversion unit 107. Unreacted ethylene stream 20 and unreacted 2-butene stream 21 may be recycled back to olefin conversion unit 107. According to embodiments of the invention, a conversion rate of 2-butene and 1-butene collectively from the MTBE raffinate may be in a range of 50 to 78% and all ranges and values therebetween, including ranges of 50 to 54%, 54 to 58%, 58 to 62%, 62 to 66%, 66 to 70%, 70 to 74%, or 74 to 78%.

In summary, embodiments of the invention involve a method of producing propylene using methyl tertiary butyl ether (MTBE) synthesis raffinate. By separating n-butane and isobutane from the MTBE synthesis raffinate by the molecular sieve, the concentration of 2-butene in the feed stream to the olefin conversion unit may be increased. The combined concentration of 2-butene from MTBE raffinate and 2-butene from isomerization of 1-butene may be from 94.5 wt. % to 99 wt. %. The increased concentration of 2-butene in the propylene production process may increase the efficiency of the process, thereby reducing production costs.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to

The invention claimed is:

1. A method of producing propylene, the method comprising:
   feeding methanol and $C_4$ hydrocarbons to a methyl tertiary butyl ether (MTBE) synthesis unit to react and form MTBE and unreacted $C_4$ hydrocarbons, wherein the $C_4$ hydrocarbons are provided as a byproduct stream of a steam cracker unit comprising 5 to 35 wt. % n-butane, 1 to 15 wt. % isobutane, 20 to 50 wt. % isobutylene, 10 to 35 wt. % 1-butene, 5 to 20 wt. % 2-butene, 1 to 3 wt. % of butadiene, and at least some to 1 wt. % of acetylene;
   flowing a methyl tertiary butyl ether (MTBE) synthesis raffinate stream that comprises the unreacted $C_4$ hydrocarbons through a molecular sieve so that the molecular sieve separates the MTBE synthesis raffinate stream into a stream comprising primarily n-butane and isobutane, collectively, and a stream comprising primarily 1-butene and 2-butene, collectively;
   distilling the stream comprising primarily 1-butene and 2-butene collectively to produce a first stream comprising primarily 1-butene and a first 2-butene stream comprising primarily 2-butene; and
   feeding the first stream comprising primarily 1-butene to an isomerization unit and isomerizing the 1-butene in the first stream to form a second 2-butene stream comprising primarily 2-butene;
   reacting 2-butene of the first 2-butene stream and 2-butene of the second 2-butene stream with ethylene in an olefin conversion unit to produce a first product stream comprising unreacted ethylene, unreacted 2-butene and the propylene;
   wherein the molecular sieve consists essentially of a zeolite.

2. The method of claim 1, further comprising the step of separating the first product stream into an unreacted ethylene stream comprising primarily unreacted ethylene, an unreacted 2-butene stream comprising primarily unreacted 2-butene, and a second product stream comprising primarily the propylene.

3. The method of claim 2, further comprising the step of recycling the unreacted ethylene stream and the unreacted 2-butene stream back to the olefin conversion unit.

4. The method of claim 1, wherein the molecular sieve separates 95 wt. % to 99 wt. % of 1-butene and 2-butene, collectively from the MTBE synthesis raffinate stream.

5. The method of claim 1, wherein the 1-butene and 2-butene separated by the molecular sieve collectively has a purity of 94.5 wt. %.

6. The method of claim 1, wherein the 2-butene comprises cis-2-butene and trans-2-butene.

7. The method of claim 1, wherein the isomerizing is performed in the presence of a first catalyst, and wherein the first catalyst comprises one or more transition metal elements.

8. The method of claim 1, wherein the isomerizing is performed at a first reaction temperature of 200° C.

9. The method of claim 1, wherein the zeolite is selected from the group consisting of ZSM-5, zeolite X, zeolite Y and silicalite-1, and combinations thereof.

10. The method of claim 1, wherein the zeolite is ZSM-5.

11. The method of claim 1, wherein the zeolite is silicalite-1.

12. The method claim 1, wherein the zeolite is zeolite X.

13. The method of claim 1, wherein the zeolite is zeolite Y.

14. The method of claim 1, wherein the reacting is performed at a weight hourly space velocity of 5 to 50 $hr^{-1}$.

15. The method of claim 1, wherein a conversion rate of 2-butene and 1-butene collectively from the MTBE synthesis raffinate stream is in a range of 50 to 78%.

16. The method of claim 1, wherein the molecular sieve is loaded on a π complexing adsorbent, and
   wherein the π complexing adsorbent comprises:
      a support material selected from the group of consisting of aluminosilicates, silica, alumina, a mesoporous material, and combinations thereof, wherein the mesoporous material comprises mesoporous silicas selected from the group consisting of SBA-15, SBA-16 and TUD-1 framework type material, and combinations thereof; and
      a compound supported on the support material, wherein the compound is selected from the group consisting of $CuNO_3$, $Cu(NO_3)_2$ and $Fe(NO_3)_2$, and combinations thereof.

17. The method of claim 1, wherein the molecular sieve is loaded on a π complexing adsorbent, wherein the π complexing adsorbent comprises $Fe(NO_3)_2$ supported on a support material.

18. A method of producing propylene, the method comprising:
   feeding methanol and $C_4$ hydrocarbons to a methyl tertiary butyl ether (MTBE) synthesis unit to react and form MTBE and unreacted $C_4$ hydrocarbons, wherein the $C_4$ hydrocarbons are provided as a byproduct stream of a steam cracker unit comprising 5 to 35 wt. % n-butane, 1 to 15 wt. % isobutane, 20 to 50 wt. % isobutylene, 10 to 35 wt. % 1-butene, 5 to 20 wt. % 2-butene, 1 to 3 wt. % of butadiene, and 0 to 1 wt. % of acetylene;
   flowing a methyl tertiary butyl ether (MTBE) synthesis raffinate stream that comprises the unreacted $C_4$ hydrocarbons through a molecular sieve so that the molecular sieve separates the MTBE synthesis raffinate stream into a stream comprising primarily n-butane and isobutane, collectively, and a stream comprising primarily 1-butene and 2-butene, collectively;
   distilling the stream comprising primarily 1-butene and 2-butene collectively to produce a first stream comprising primarily 1-butene and a first 2-butene stream comprising primarily 2-butene;
   isomerizing the 1-butene in the first stream to form a second 2-butene stream comprising primarily 2-butene; and
   reacting 2-butene of the first 2-butene stream and 2-butene of the second 2-butene stream with ethylene to produce the propylene;
   wherein the molecular sieve is loaded on a π complexing adsorbent, wherein the π complexing adsorbent comprises $Fe(NO_3)_2$ supported on a support material.

19. A method of producing propylene, the method comprising:
   feeding methanol and $C_4$ hydrocarbons to a methyl tertiary butyl ether (MTBE) synthesis unit to react and form MTBE and unreacted $C_4$ hydrocarbons,
   flowing a methyl tertiary butyl ether (MTBE) synthesis raffinate stream that comprises the unreacted $C_4$ hydrocarbons through a molecular sieve so that the molecular sieve separates the MTBE synthesis raffinate stream into a stream comprising primarily n-butane and isobutane, collectively, and a stream comprising primarily 1-butene and 2-butene, collectively;
distilling the stream comprising primarily 1-butene and 2-butene collectively to produce a first stream comprising primarily 1-butene and a first 2-butene stream comprising primarily 2-butene;
isomerizing the 1-butene in the first stream to form a second 2-butene stream comprising primarily 2-butene; and
reacting 2-butene of the first 2-butene stream and 2-butene of the second 2-butene stream with ethylene to produce the propylene;
wherein the molecular sieve is loaded on a π complexing adsorbent, wherein the π complexing adsorbent comprises $Fe(NO_3)_2$ supported on a support material.

* * * * *

UNITED STATES PATENT AND TRADEMARK OFFICE
CERTIFICATE OF CORRECTION

PATENT NO. : 11,505,516 B2
APPLICATION NO. : 16/631633
DATED : November 22, 2022
INVENTOR(S) : Guillermo Leal et al.

It is certified that error appears in the above-identified patent and that said Letters Patent is hereby corrected as shown below:

In the Claims

At Column 11, Claim number 1, Line number 26, delete "and".
At Column 11, Claim number 1, Line number 30, add --and-- after "primarily 2-butene;".

Signed and Sealed this
Twenty-eighth Day of February, 2023

Katherine Kelly Vidal
*Director of the United States Patent and Trademark Office*